United States Patent [19]
Cooke et al.

[11] 3,981,890
[45]* Sept. 21, 1976

[54] 2-(N-THIOCARBAMOYL-N-SUBSTITUTED-AMINO)-3,4-METHYLENEDIOXY BENZHYDROLS

[75] Inventors: George A. Cooke, Denville; William J. Houlihan, Mountain Lakes, both of N.J.

[73] Assignee: Sandoz, Inc., E. Hanover, N.J.

[ * ] Notice: The portion of the term of this patent subsequent to Apr. 1, 1992, has been disclaimed.

[22] Filed: Jan. 20, 1975

[21] Appl. No.: 542,216

Related U.S. Application Data

[60] Division of Ser. No. 343,817, March 22, 1973, Pat. No. 3,875,093, which is a continuation of Ser. No. 141,011, May 6, 1971, abandoned.

[52] U.S. Cl. .............. 260/340.5; 260/329 S; 260/332.3 P; 260/332.3 H; 260/332.5
[51] Int. Cl.$^2$ .............................. C07D 317/44
[58] Field of Search .................. 260/340.5, 329 S

[56] References Cited
UNITED STATES PATENTS

| | | | |
|---|---|---|---|
| 3,748,331 | 7/1973 | Cooke et al. | 260/340.5 X |
| 3,876,665 | 4/1975 | Cooke et al. | 260/340.5 |

Primary Examiner—Ethel G. Love
Attorney, Agent, or Firm—Gerald D. Sharkin; Richard E. Vila

[57] ABSTRACT

1,4 disubstituted-methylenedioxy-quinazoline-2(1H)-thiones are provided which are useful as pharmaceutical agents, e.g. anti-inflammatory agents. The title compounds are intermediates in their preparation.

2 Claims, No Drawings

2-(N-THIOCARBAMOYL-N-SUBSTITUTED-AMINO)-3,4-METHYLENEDIOXY BENZHYDROLS

This is a division of application Ser. No. 343,817, filed Mar. 22, 1973, now U.S. Pat. No. 3,875,093, which, in turn, is a continuation of Ser. No. 141,011 filed May 6, 1971, and now abandoned.

This invention relates to 2(1H)-quinazolin-thiones and their preparation.

More particularly, this invention provides novel compounds of formula I,

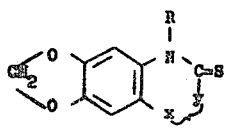

in which

R signifies an alkyl radical of 1 to 5 carbon atoms, e.g. methyl, ethyl, isopropyl and t-butyl; cyclo(lower)alkyl of 3 to 6 carbon atoms, e.g. cyclopropyl and cyclohexyl; or cyclo(lower)alkyl(lower) straight chain alkyl of 4 to 7 total carbon atoms in which the cycloalkyl is of 3 to 6 carbon atoms and the straight chain alkyl is of 1 to 3 carbon atoms, e.g. cyclopropylmethyl; and

signifies a group

or

in which $R_1$ signifies a radical of formula II,

or of formula III,

in which either Y and $Y_1$ are the same or different and signify a hydrogen, fluorine or chlorine atom, an alkyl or alkoxy radical of 1 to 3 carbon atoms, or a nitro or trifluoromethyl group, provided that no more than one of Y and $Y_1$ signifies a trifluoromethyl or nitro group, or Y and $Y_1$ are on adjacent carbon atoms and together signify a methylenedioxy group, and $Y_2$ signifies a hydrogen, fluorine or chlorine atom, or an alkyl radical of 1 to 3 carbon atoms.

The invention also provides processes for the production of compounds of formula I characterized by a. producing a compound of formula Ia,

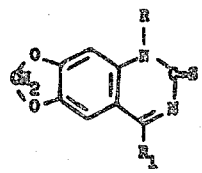

in which R and $R_1$ are as defined above, by reacting at elevated temperature a compound of formula IV

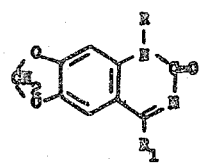

in which R and $R_1$ have the significance stated above, with phosphorous pentasulpihide, in the presence of an organic solvent which is inert under the reaction conditions, or b. producing a compound of formula Ia, stated above, by cyclizing a compound of formula V,

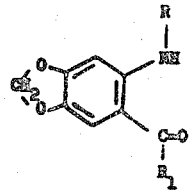

in which R and $R_1$ are as defined above, either (i) by reaction with an acid chloride or bromide and an isothiocyanate of formula VI,

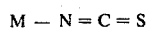

in which M signifies an alkali metal or alkaline earth metal cation, or the ammonium cation, or with the reaction product of an acid chloride or bromide and an isothiocyanate of formula VI, stated above, or (ii) with isothiocyanic acid, or c. producing a compound of formula Ib

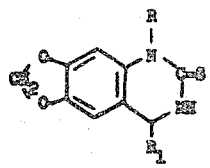

in which R and $R_1$ are as defined above, by cyclizing a compound of formula VII,

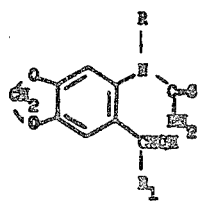

in which R and R₁ are as defined above, by removal of the elements of water.

Process (a) is preferably effected at a temperature of from about 70° to about 180°C., more preferably from 100° to 130°C., and conveniently at a reflux temperature of the reaction medium, in an organic solvent which is inert under the reaction conditions. Suitable organic solvents include pyridine, toluene and xylene, of which pyridine is preferred since it appears to have a beneficial effect on the rate of reaction. Reaction time may vary for example from 1 to 50 hours, more typically from 10 to 30 hours.

Process (b) (i) is conveniently effected in an organic solvent which is inert under the reaction conditions, at a temperature of from 10° to 80°C., preferably 30° to 70°C. As indicated, the process may be effected by reacting a compound of formula V with the reaction product of an acid chloride or bromide and an isothiocyanate of formula VI and it is generally preferred to first react the acid halide and compound of formula VI and then add the compound of formula V to the resulting reaction mixture. The reaction of the acid halide and compound VI is exothermic and is preferably initiated at a temperature of from 10°C. to 30°C. It will be understood that the acid halides employed should not carry substituents or functional groups which would interfere with the process. Suitable acid halides include acetyl chloride and benzoyl chloride, preferably benzoyl chloride. Naturally, the most suitable compounds of formula VI are those most readily reacting with the acid halide to eliminate as a by-product a halide of the cation M. Suitably, the compound of formula VI is an alkali metal isothiocyanate such as sodium isothiocyanate or ammonium isothiocyanate, and preferably ammonium isothiocyanate. Suitable solvents include lower alcohols, ketones and cyclic ethers, acetone being preferred.

Process (b) (i) is particularly suitable for the preparation of compounds of formula Ia in which Y and/or Y₁ is other than an orthosubstituent.

Process (b) (ii) is suitably effected at a temperature of from 50° to 150°C., preferably 100° to 140°C. Isothiocyanic acid is well known to be unstable and is therefore desirably prepared in situ. Thus the process may be effected in acidic medium employing a salt of isothiocyanic acid of formula VI stated above.

Process (c) is preferably carried out at an elevated temperature and under acidic conditions. Suitable temperatures are for example from 80° to 150°C., preferably 95° to 120°C. The acid employed in the dehydration is desirably a strong inorganic acid such as sulfuric acid or hydrochloric acid, or an organic acid such as acetic acid, more preferably the latter. Water may be employed as the sole reaction medium although various co-solvents, e.g. ethanol, may also be used, if desired or required to insure optimum solubility.

Process (c) is a reaction of a type described in the literature, for example, J. Chem. Soc. 1959, 3555.

The compounds of formula VII, employed as starting materials in process (c), may be produced by reacting isothiocyanic acid with a compound of the formula VIII:

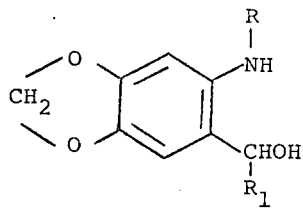

VIII wherein R and R₁ are as defined.

The reaction is desirably carried out in acidic aqueous medium at a controlled temperature of from 0° to about 80°C., preferably from 15° to 35°C. The isothiocyanic acid is preferably formed in situ by effecting the reaction in acidic medium and employing a salt of isothiocyanic acid of formula VI, stated above. The compound of formula VI is suitably an alkali metal, e.g. sodium or potassium, an alkaline earth metal, e.g. calcium, or ammonium isothiocyanate and is preferably potassium isothiocyanate. The acid employed to provide the acidic reaction medium and produce in situ the desired isothiocyanic acid is, for example sulfuric acid or hydrochloric acid, or an organic acid such as acetic acid, more preferably the latter.

The compounds of formula VIII used for producing compounds of formula VII above, may be produced in manner known per se, e.g. by reduction of a compound of formula V, stated above, for example with sodium borohydride, in an organic solvent which is inert under the reaction conditions, as described by G. N. Walker, J. Org. Chem 27, 1929 (1962).

Unless otherwise indicated, the various intermediate products described herein, may be isolated and purified using conventional techniques.

The compounds of formula I possess pharmaceutical activity in animals. In particular, the compounds are useful as anti-inflammatory agents as indicated by the Carrageenan-induced edema test in rats. For such use, the compounds may be combined with a pharmaceutically acceptable carrier, and other conventional adjuvants, and preferably administered orally in such forms as tablets, capsules, elixirs, suspensions and the like. For the above-mentioned use, the dosage administered will vary depending upon known factors such as the particular compound used and mode of administration. However, in general, the compounds of formula Ia provide satisfactory results when administered at a daily dose of from about 0.2 milligrams to 180 milligrams per kilogram of body weight, preferably given in divided doses 2 to 4 times a day, with daily dosage for large mammals ranging from between about 16 milligrams to 1500 milligrams and individual doses between 4 milligrams to 750 milligrams. The compounds of formula Ib, in general, provide satisfactory results when administered at a daily dose of from about 3 milligrams to 250 milligrams per kilogram of body weight, preferably given in divided doses, with daily dose for large mammals ranging between about 200 milligrams to 2500 milligrams and individual doses ranging between 50 to 1250 milligrams.

The compounds of the formula I, particularly Ia, are also useful as analgesics, as indicated by application of pressure to yeast-inflamed foot of the rat (oral administration), and as anti-pyretics as indicated by inhibition of yeast-induced fever in rats (oral administration). For such uses, the compounds may be administered in modes and forms similar to those employed in the treatment of inflammation and at dosages indicated above as applicable for the use of the compound in the treatment of inflammation.

The compounds may be administered orally in such forms as tablets, dispersible powders, granules, capsules, elixirs, suspensions and syrups, or parenterally in the form of an injectable solution or suspension. Such compositions may be prepared according to any method known in the art for the manufacture of pharmaceutical compositions, and such compositions may contain one or more conventional adjuvants, such as sweetening agents, flavouring agents, colouring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient along or admixed with an inert solid diluent, e.g., calcium carbonate, calcium phosphate and kaolin. The preferred pharmaceutical compositions from the stand-point of preparation and ease of administration are solid compositions, particularly hard-filled capsules and tablets.

The intermediates of the formula X are also useful because they exhibit pharmacological activity in animals. In particular, the compounds of the formula X are useful as anti-inflammatory agents as indicated by the Carrageenan-induced edema test in rats. Such compounds, which may be administered in modes and forms similar to the compounds of formula I, generally provide satisfactory anti-inflammatory results when administered at a daily dose of from 2 to 200 milligrams per kilogram of animal body weight with daily dosage for large mammals being in the range between about 140 to 2000 milligrams and divided doses between 35 and 1000 milligrams.

A representative formulation is a capsule prepared by conventional techniques and containing the following ingredients:

| Ingredient | Parts by Weight |
| --- | --- |
| Compound of formula I, e.g. 1-isopropyl-4-phenyl-6,7-methylene-dioxy-2(1H)-quinazolinthione | 50 |
| Inert solid diluent e.g. kaolin | 200 |

Preferred compounds of formula I from the point of view of pharmacological activity, are the compounds of formula Ia, particularly those in which R signifies an isopropyl radical, for example, 1-isopropyl-4-phenyl-6,7-methylenedixoy-2(1H)-quinazolinthione.

As used herein, the expression "in manner known per se" means methods in use or described in the literature on the subject.

The following example illustrates the invention. Unless otherwise stated, percentages are by weight and temperatures are in degrees Centigrade.

EXAMPLE 1

Step A

Preparation of 2-isopropylamino-4,5-methylenedioxybenzohydrol

To a flask equipped with a stirrer and condenser are charged 5.09 g. of 2-isopropylamino-4,5-methylenedi-oxybenzophenone (prepared in Example 5) and 125 ml. of methanol. The stirred solution is treated portionwise (ca. 15 minutes) with 2.5 g. of sodium borohydride. The resulting mixture is stirred at room temperature for ca. 12 hours and then concentrated in vacuo. The residue is treated with 100 ml. of water and then extracted with two 50 ml. portions of $CH_2Cl_2$. The organic layer is dried with anhydrous $Na_2SO_4$, filtered and concentrated. Upon recrystallization from ether, there is obtained 2-isopropylamino-4,5-methylenedioxybenzohydrol, which melts at 78°–80°C.

Step B

Preparation of 1-isopropyl-4-phenyl-6,7-methylenedioxy-3,4-dihydro-2[1H]-quinazolinthione To a solution of 1 gram of 2-isopropylamino-4,5-methylenedioxybenzhydrol and 28 mls. glacial acetic acid is added 2 grams of ammonium thiocyanate. The resultant mixture is stirred at room temperature for 24 hours to solid precipitates and is removed by filtration. The filtrate is evaporated to dryness and the residual solid taken up in chloroform. This solution is washed with water, dried and evaporated to dryness. The resulting solid is recrystallized from ethyl acetate to yield 1-isopropyl-4-phenyl-6,7-methylenedioxy-3,4-dihydro-2[1H]-quinazolinthione m.p. 214°–218°C.

We claim:

1. The compound of the formula:

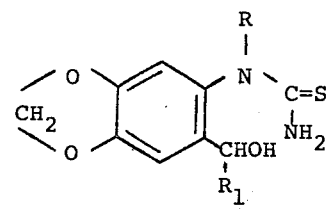

in which
R is alkyl of 1 to 5 carbon atoms, cycloalkyl of 3 to 6 carbon atoms or cycloalkylalkyl in which the cycloalkyl portion is of 3 to 6 carbon atoms and the alkyl is straight chain alkyl of 1 to 3 carbon atoms, and $R_1$ is

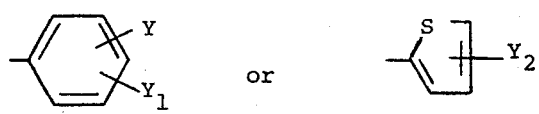

in which Y and $Y_1$ are the same or different and are hydrogen, fluoro, chloro, alkyl of 1 to 3 carbon atoms, alkoxy of 1 to 3 carbon atoms, nitro or trifluoromethyl, provided that no more than one of Y and $Y_1$ are trifluoromethyl or nitro, or Y and $Y_1$ are on adjacent carbon atoms and together form a methylenedioxy, and $Y_2$ is hydrogen, fluoro, chloro or alkyl radical of 1 to 3 carbon atoms.

2. A compound of claim 1 in which $R_1$ is

* * * * *